United States Patent [19]
Nomikos et al.

[11] Patent Number: 5,153,900
[45] Date of Patent: Oct. 6, 1992

[54] MINIATURIZED LOW POWER X-RAY SOURCE

[75] Inventors: Peter M. Nomikos, London, England; Mark T. Dinsmore, Sudbury; Alan P. Sliski, Lincoln, both of Mass.

[73] Assignee: Photoelectron Corporation, Waltham, Mass.

[21] Appl. No.: 577,883

[22] Filed: Sep. 5, 1990

[51] Int. Cl.⁵ ............................................. A61N 5/10
[52] U.S. Cl. .................................... 378/65; 378/64; 378/119; 378/110; 378/96
[58] Field of Search ............... 378/119, 121, 124, 137, 378/138, 145, 91, 93, 101, 102, 103, 113, 110, 65, 64, 99, 96, 97, 108, 109, 112, 114, 117, 111; 600/1, 2

[56] References Cited

U.S. PATENT DOCUMENTS

| | | | |
|---|---|---|---|
| 1,981,583 | 10/1929 | Craig | 99/11 |
| 2,748,293 | 5/1956 | Reiniger | 378/65 |
| 3,714,486 | 1/1973 | McCrary | 313/55 |
| 3,920,999 | 11/1975 | Drexler et al. | 250/493 |
| 4,104,531 | 8/1978 | Weiss | 250/490 |
| 4,104,532 | 8/1978 | Weiss | 250/490 |
| 4,109,154 | 8/1978 | Taumann | 250/503 |
| 4,117,334 | 9/1978 | Strauts | 250/402 |
| 4,157,475 | 6/1979 | Stock et al. | 250/503 |
| 4,205,251 | 5/1980 | Zwep | 313/330 |
| 4,344,181 | 8/1982 | Baecklund | 378/45 |
| 4,517,472 | 5/1985 | Ruitberg et al. | 307/82 |
| 4,563,769 | 1/1986 | Madsen | 378/121 |
| 4,646,338 | 2/1987 | Skillicorn | 378/110 |
| 4,694,480 | 9/1987 | Skillicorn | 378/119 |
| 4,789,997 | 12/1988 | Madsen et al. | 378/109 |
| 4,856,036 | 8/1989 | Malcolm et al. | 378/116 |
| 4,924,485 | 5/1990 | Hoeberling | 378/102 |

*Primary Examiner*—Janice A. Howell
*Assistant Examiner*—Don Wong
*Attorney, Agent, or Firm*—Lahive & Cockfield

[57] ABSTRACT

A low-level, electron beam activated source of preselected or programmable duration and intensity x-rays. The source may be fully or partially implanted into, or surface-mounted onto a desired area to affect a preselected irradiated region. In medical applications, a method of treating malignant cells, such as tumors, in vivo, utilizing the apparatus described above.

33 Claims, 5 Drawing Sheets

MINIATURIZED LOW POWER X-RAY SOURCE

BACKGROUND OF DISCLOSURE

The present invention relates to a miniaturized, low power, programmable x-ray source for use in delivering low-levels of substantially constant or intermittent x-rays to a specified region Conventional medical x-ray sources are large, fixed position machines. Generally, the head of the x-ray tube is placed in one room and the control console in an adjoining area, with a protective wall, equipped with a viewing window, separating the two. The x-ray tube typically is approximately 20 to 35 centimeters (cm) long, and approximately 15 cm in diameter. A high voltage power supply is housed within a container located in a corner of the room containing the x-ray tube. Patients are brought to the machine for diagnostic, therapeutic, or palliative treatment.

Diagnostic x-ray machines are typically operated at voltages below 150 kilovolts (kV), and at currents from approximately 25 to 1200 milliamps (mA). By contrast, the currents in therapeutic units typically do not exceed 20 mA at voltages which may range above 150 kV. When an x-ray machine is operated at nominal voltages of 10 to 140 kV, the emitted x-rays provide limited penetration of tissue, and are thus useful in treating skin lesions. At higher voltages (approximately 250 kV), deep x-ray penetration is achieved, which is useful in the treatment of major body tumors. Supervoltage machines, operable in the 4 to 8 megavolt (MV) region, are used to ablate or destroy all types of tumors, except superficial skin lesions.

A conventional x-ray tube includes an anode, grid, and cathode assembly. The cathode assembly generates an electron beam which is directed to a target, by an electric field established by the anode and grid. The target in turn emits x-ray radiation in response to the incident electron beam. The radiation absorbed by a patient generally is that which is transmitted from the target in the x-ray tube through a window in the tube, taking into account transmission losses. This window typically is a thin section of beryllium, or other suitable material. In a typical x-ray machine, the cathode assembly consists of a thoriated tungsten coil approximately 2 mm in diameter and 1 to 2 cm in length which, when resistively heated with a current of 4 amps (A) or higher, thermionically emits electrons. This coil is surrounded by a metal focussing cup which concentrates the beam of electrons to a small spot on an opposing anode which also functions as the target. In models having a grid, it is the grid which both controls the path of the electron beam and focuses the beam.

The transmission of an electron beam from cathode to anode is influenced by electron space charge forces which tend to become significant in conventional x-ray machines at currents exceeding 1 A. In such conventional machines, the beam is focussed on the anode to a spot diameter ranging anywhere from 0.3 to 2.5 millimeters (mm). In many applications, most of the energy from the electron beam is converted into heat at the anode. To accommodate such heating, high power medical x-ray sources often utilize liquid cooling and a rapidly rotating anode, thereby establishing an increased effective target area, permitting a small focal spot while minimizing the effects of localized heating. To achieve good thermal conductivity and effective heat dissipation, the anode typically is fabricated from copper. In addition, the area of the anode onto which an electron beam is incident requires a material of high atomic number for efficient x-ray generation. To meet the requirements of thermal conductivity, effective heat dissipation, and efficient x-ray generation, a tungsten alloy typically is embedded in the copper.

In use, the total exposure from an x-ray source is directly proportional to the time integral of the electron beam. During relatively long exposures (e.g. lasting 1 to 3 seconds), the anode temperature may rise sufficiently to cause it to glow brightly, accompanied by localized surface melting and pitting which degrades the radiation output. However, thermal vaporization of the tube's coiled cathode filament is most frequently responsible for conventional tube failure.

While the efficiency of x-ray generation is independent of the electron beam current, it is highly dependent on the acceleration voltage. Below 60 kV, only a few tenths of one percent of the kinetic energy from an electron is converted to x-rays, whereas at 20 MV that conversion factor rises to 70 percent. An emitted x-ray spectrum is composed in part of discrete energies characteristic of transitions between bound electron energy levels of the target element. The spectrum also includes an x-ray energy continuum, known as bremsstrahlung, which is caused by acceleration of the beam electrons as they pass near target nuclei. The maximum energy of an x-ray cannot exceed the peak energy of an electron in the beam. Further, the peak of the bremsstrahlung emission curve occurs at approximately one-third the electron energy.

Increasing the electron current results in a directly proportional increase in x-ray emission at all energies. However, a change in beam voltage results in a total x-ray output variation approximately equal to the square of the voltage, with a corresponding shift in peak x-ray photon energy. The efficiency of bremsstrahlung radiation production increases with the atomic number of the target element. The peak output in the bremsstrahlung curve and the characteristic spectral lines shift to higher energies as the atomic number of the target increases. Although tungsten ($Z=74$) is the most common target material used in modern tubes, gold ($Z=79$) and molybdenum ($Z=42$) are used in some specialty tubes.

X-rays interact in several ways with matter. For biological samples, the following two types of interactions are most important: Compton scattering of moderate-energy x-rays with outer shell electrons; and, photoionizing interactions of inner shell electrons. In these processes, the probability of atom ionization decreases with increasing photon energy in both soft tissue and bone. For the photoelectric effect, this relationship follows an inverse third-power law.

One disadvantage of present x-ray devices used for therapy is the high voltage required when directed to soft tissue within or beneath bone. One example is in directing x-rays to areas of the human brain, which is surrounded by bone. High energy x-rays are required to penetrate the bone, but often damage the skin and brain tissue. Another example in radiation therapy is in directing the x-rays to soft tissue located within the body cavity, couched among other soft tissue, or within an internal calciferous structure. Present high-voltage machines are limited in their ability to selectively provide desired x-ray radiation to such areas.

Another disadvantage of the high voltage output of present x-ray sources is the damage caused to skin external to the affected organ or tissue. Therefore, high voltage devices of present systems often cause significant damage not only to the target region or tissue, but also to all surrounding tissue and surface skin, particularly when used for human tumor therapy. However, since present devices apply x-ray radiation to target regions internal to a patient from a source external to the target region, such incidental tissue damage is practically unavoidable.

An alternative form of tumor therapy involves implanting encapsulated radioisotopes in or near the tumor to be treated. While such use of radioisotopes may be effective in treating certain types of tumors, introduction of the isotopes requires invasive procedures which have potential side-effects, such as the possibility of infection. Moreover, brain swelling may occur in some applications because the emission from the isotope cannot be controlled. Further, there is no ability to provide selective control of time dosage or radiation intensity. Handling and disposal of such radioisotopes involves hazards to both the individual handler and the environment.

In another application, x-ray radiation is often used to inspect materials in support of structural analysis and manufacturing processes, particularly in the semiconductor chip manufacturing industry. X-ray machines for such applications are large, fixed-position machines often incorporated into the manufacturing assembly line. These cumbersome machines not only take up much physical space, but make the use of x-ray imaging impractical in many, otherwise useful, applications.

In view of the above requirements and limitations to the use of x-rays from present machines in therapeutic, diagnostic, palliative, or evaluative environments, there remains a need for a relatively small, easily manipulated, low-energy, x-ray device. Such a device operating at low energy and power will be suitable for many of the applications described herein.

Thus, it is an object of the present invention to provide an easily manipulated, low-power x-ray device.

It is another object of the invention to provide a relatively small, low-power x-ray device having a controllable, or programmable, power supply.

It is another object of the invention to provide a relatively small, low-power x-ray device which is implantable into a patient for directly irradiating a desired region of tissue with x-rays.

It is yet another object of the invention to provide a relatively small, surface-mountable, low-power x-ray device for affecting a desired surface region with x-rays.

It is yet another object of the invention to provide a relatively small, low-power x-ray device which is partially implantable into a patient for directly irradiating a specified region with x-rays.

SUMMARY OF THE INVENTION

Briefly, the invention is an easily manipulated apparatus having a low-level, electron beam (e-beam) activated x-ray source of preselected, or adjustable, duration and intensity. In medical applications, the apparatus may be fully or partially implanted into, or surface-mounted onto a desired area of a host to irradiate a preselected region with x-rays.

The apparatus operates at a relatively low voltage, for example, in the range of approximately 10 kV to 90 kV, with small electron currents, for example, in the range of from approximately 1 nA to 100 $\mu$A. To achieve a desired radiation pattern over a desired region, while minimally irradiating other regions, x-rays may be emitted from a nominal, or effective "point" source located within or adjacent to the desired area to be affected. A low dose rate of x-rays irradiates any part of the desired region, either continually or periodically, over extended periods of time.

The apparatus may include a controllable, or programmable, power supply located outside the desired region to enable variations in voltage, current, and timing of x-ray radiation. The target, or x-ray emitting, material may be tailored in its composition and/or geometry to provide a customized pattern of x-rays. Shielding at the emission site, or around the target, further enables control of the energy and spatial profile of the x-ray emission to match the preselected distribution of radiation throughout the desired region.

The present invention further provides a method of treating malignant cells, such as found in tumors, in vivo. utilizing the apparatus described above. Generally, the method involves identifying and locating malignant cells with a device generally available in the art, such as by computer-aided tomography (CAT) scan or magnetic resonance imaging (MRI). Then, a low-power electron beam source and a selectively shaped x-ray radiation pattern generating target and shield assembly are positioned proximate to the malignant cells, the target and shield assembly geometry and materials being shaped and selected in accordance with the characteristics of the malignant cells. A programmable power supply is provided, which may be used to vary the voltage, current, and duration of the electron beam source to establish a desired electron beam which is directed to the target. Finally, x-rays emitted from the target and shield assembly are introduced into the malignant cells for selective destruction of the cells.

BRIEF DESCRIPTION OF DRAWINGS

The foregoing and other objects of this invention, the various features thereof, as well as the invention itself, may be more fully understood from the following description, when read together with the accompanying drawings in which:

FIG. 8A is a cross-section view of the assembly of FIG. 8, taken along lines 8a.

Like numbered elements in each FIGURE represent the same or similar elements.

DESCRIPTION OF THE PREFERRED EMBODIMENTS

The present invention is a relatively small, electron-beam activated, low power x-ray apparatus. The apparatus may be used for medical purposes, for example, therapeutic or palliative radiation treatment of tumors, or for other purposes, such as monitoring structural integrity of materials or as a radiation source for use in analytical instruments.

With particular regard to medical uses, the apparatus may be fully implanted or partially inserted into a preselected internal region of a patient to provide low dose rate x-ray radiation over selected exposure times. Alternately, the apparatus may be mounted on a surface of a patient external to a region to be irradiated. Also disclosed is a method for treating tumors in a patient, using the apparatus of the invention.

Generally, the apparatus of the present invention includes an electron-beam (e beam) activated x-ray source which operates at relatively low voltages, i.e. in the range of approximately 10 kV to 90 kV, and relatively small electron beam currents, i.e. in the range of approximately 1 nA to 100 $\mu$A. At those operating voltages and currents, the x-ray output is relatively low, and the apparatus may be made quite small and be adapted for implantation in medical therapeutic applications. In view of the low level x-ray output, adequate tissue penetration and cumulative dosage may be attained by locating the x-ray source adjacent to or within the region to be irradiated. Thus, the x-rays are emitted from a well-defined, small source located within or adjacent to the region to be irradiated. In the preferred embodiment, a low dose rate of x-rays may be applied to any part of a tumor, either continually or periodically, over extended periods of time, e.g., up to one month. This is in contrast to short pulses of higher doses applied from points remote from the desired location, as provided by currently available x-ray diagnostic and therapeutic apparatus.

The present invention provides interstitial radiotherapy similar to that achieved with implanted capsules, needles, tubes, and threads containing natural or artificial radioactive isotopes, known as brachytherapy. However, a programmable power supply may be included in the x-ray source of the present apparatus to vary voltage, current, and duration of the radiation. This differs from brachytherapy in that the intensity and penetration depth of the x-rays may be changed without surgically or invasively replacing the isotopes. Furthermore, the present invention is not limited by the half-life of a particular isotope, and does not pose a radiation hazard when turned off.

Figure 1:
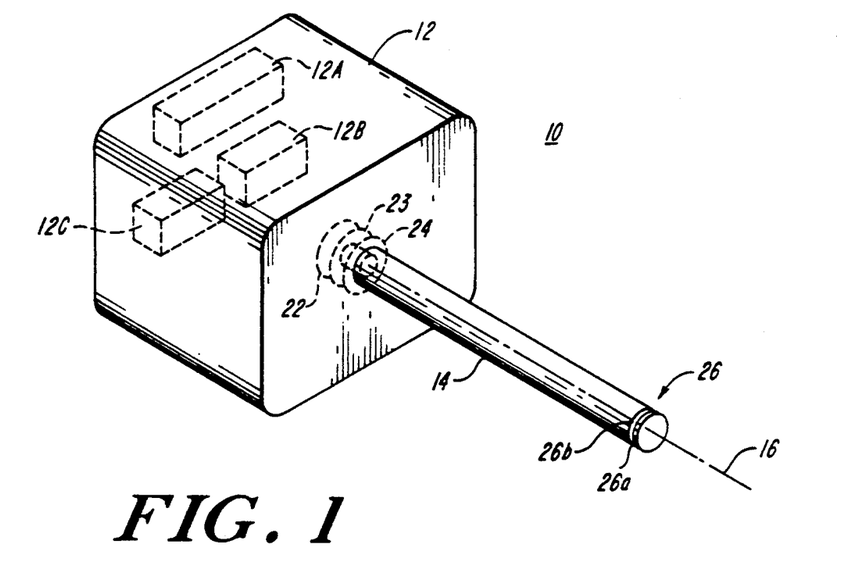
FIG. 1 is a perspective view of a low power x-ray source embodying the present invention.

FIG. 1 shows an x-ray apparatus 10 embodying the present invention. Apparatus 10 includes a housing 12 and an elongated cylindrical probe 14 extending from housing 12 along a reference axis 16. The housing 12 encloses a high voltage power supply 12A (illustrated in electrical schematic form in FIGS. 6 and 7). The probe 14 is a hollow tube having an electron beam generator (cathode) 22 adjacent to the high voltage power supply 12A. Cathode 22 is located in close proximity to an annular focussing electrode 23 typically at the same potential as the cathode 22. An annular anode 24 is positioned approximately 0.5 cm or more from the annular focussing electrode 23. A hollow, tubular probe 14 extends along the same axis as the cathode, grid, and the hole in the anode. Probe 14 is integral with the housing 12 and extends toward a target assembly 26. In various embodiments, parts of the probe 14 may be selectively shielded to control the spatial distribution of x-rays. In addition, the probe 14 may be magnetically shielded to prevent external magnetic fields from deflecting the beam away from the target.

The electron beam generator 22 may include a tungsten filament thermionic emitter (driven by a floating low voltage power supply) or a photocathode (irradiated by an LED or laser source). The high voltage power supply establishes an acceleration potential difference between the cathode of generator 22 and the grounded anode 24 so that an electron beam is established along the reference axis 16, through the center hole of the anode and to the target assembly 26, with the region between anode 24 and the target assembly 26 being substantially field free. The beam generation and acceleration components are adapted to establish a thin (e.g. 1 mm or less in diameter) electron beam within the probe 14 along axis 16.

In a preferred embodiment, the probe 14 is a hollow, evacuated beryllium (Be), tantalum (Ta) or stainless steel cylinder 15 cm long with an interior diameter of 2 mm, and an exterior diameter of 3 mm. The target assembly 26 includes an emission element consisting of a small beryllium (Be) disc 26a coated on the side exposed to the incident electron beam with a thin film or layer 26b of tungsten (W). By way of example, with electrons accelerated to 30 keV—, a 2.2 micron thick tungsten film absorbs substantially all the incident electrons, while transmitting approximately 95% of any 30 keV—, 88% of any 20 keV—, and 83% of any 10 keV— x-rays generated in that layer. In the preferred embodiment, the beryllium substrate disc is 1 mm thick with the result that 95% of these x-rays generated in directions normal and toward the substrate, and having passed through the tungsten target, are then transmitted through the beryllium substrate and outward at the distal end of probe 14.

In some forms of the invention, the disc 26a assembly may include a multiple layer film 26b, where the differing layers may have different emission characteristics. By way of example, the first layer may have an emission (vs. energy) peak at a relatively low energy, and the second (underlying) layer may have an emission (vs. energy) peak at a relatively high energy. With this form of the invention, low energy electrons from the beam may be used to generate x-rays in the first layer (to achieve a first radiation characteristic) and high energy electrons may be used to penetrate through to the underlying layer (to achieve a second radiation characteristic). As an example, a 0.5 mm wide electron beam is emitted at the cathode and accelerated to 30 keV— through the anode, with 0.1 eV transverse electron energies, and arrives at the target 26 ten centimeters downstream from the anode, with a beam diameter of less than 1 mm at the target. X-rays are generated in the target material in accordance with preselected beam voltage, current, and target composition. The x-rays thus generated pass through the beryllium disc 26a in the probe with minimized loss in energy. The disc 26a may be made of carbon, beryllium (Be), or other suitable material which permits x-rays to pass with a minimum loss of energy. An optimal material for disc 26a is diamond, since that material is an excellent heat conductor. In some embodiments, a discrete x-ray transmissive window separate from the target assembly 26 may be used. Using these parameters, the resultant x-rays have sufficient energy to penetrate into soft tissues to a depth of a centimeter or more, the exact depth dependent upon the x-ray energy distribution.

The apparatus of FIG. 1 is particularly adapted for full implantation into a patient, where the housing 12 has a biocompatible outer surface and encloses both a high voltage power supply circuit 12A for establishing a drive voltage for the beam generator 22, and an associated battery 12B for driving that circuit 12A. In this case, an associated controller 12C establishes control of the output voltage of the high power supply circuit 12A, in the manner described below.

The apparatus of FIG. 1 may also be used in a manner where only the probe 14 is inserted into a patient while the housing remains outside the patient, i.e., a transcutaneous form. In the latter form, the various elements shown within housing 12 may alternatively be remotely located.

Figure 2:
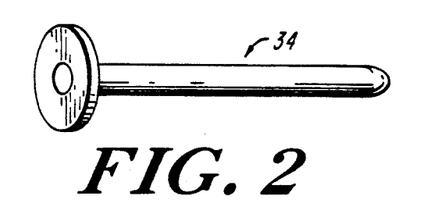
FIG. 2 is a schematic representation of a sheath adapted for use with the apparatus of FIG. 1.

In the transcutaneous form, the apparatus 10 may be used with an elongated closed end (or cup-shaped) sheath 34, as shown in FIG. 2, having a biocompatible outer surface, for example, fabricated of medical grade aliphatic polyurethane, as manufactured under the trademark Tecoflex® by Thermedics, Inc., Woburn, Mass. With this configuration, the sheath 34 is first inserted into the patient through a skin entry port, for example, a Demaport® port manufactured by Thermedics, Inc., Woburn, Mass. The probe 14 is then positioned within the sheath to simplify the insertion, positioning, and removal of the probe 14 from the radiation site, as desired. The lining of the sheath can be configured as an x-ray shield by introducing barium sulfate or bismuth trioxide, or other x-ray shielding materials, into the sheath. If necessary, the probe 14 and housing 12 can be secured to the patient's body to prevent any relative motion during the extended time of treatment. An exemplary sheath 34 is shown in FIG. 2.

Figure 3A:
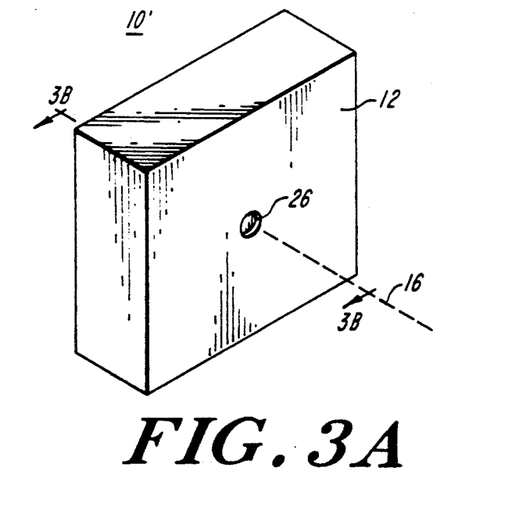
FIGS. 3A and 3B are a perspective view and sectional view, respectively, of a surface-mountable apparatus embodying the present invention.
Figure 3B:
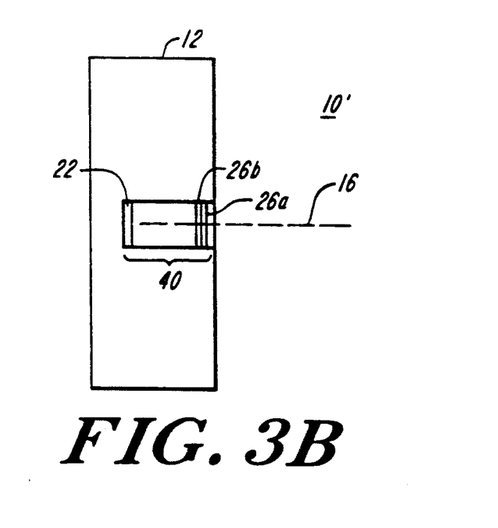

FIGS. 3A and 3B show an alternative embodiment 10' of the invention adapted for superficial usage, that is for direct placement on the skin of a patient. This form of the invention is particularly useful for x-ray treatment of skin lesions or tumors, or other dermatological applications. In FIGS. 3A and 3B, elements that correspond to elements in the embodiment of FIG. 1 are denoted with the same reference designations. Apparatus 10' generates an electron beam in a channel 40 enclosed within housing 12, where that channel 40 corresponds to probe 14. In the present embodiment, of FIGS. 3A and 3B, the target 26 (elements 26a and 26b) functions as the anode as well as an x-ray emitter. Otherwise, the apparatus 10' is similar to apparatus 10. With the configuration of FIGS. 3A and 3B, low power x-rays may be directed to a desired skin region of a patient.

In all of the above-described embodiments, the x-ray emission element of the target assembly is adapted to be adjacent to or within the region to be irradiated. The proximity of the emission element to the targeted region, e.g. the tumor, eliminates the need for the high voltages of presently used machines, to achieve satisfactory x-ray penetration through the body wall to the tumor site. The low voltage also concentrates the radiation in the targeted tumor, and limits the damage to surrounding tissue and surface skin at the point of penetration. For example, the delivery of 4000 rads, as is required after a mastectomy, with a 20 kV, 1 μA electron beam, may require approximately 40 to 50 hours of radiation. However, since the x-ray source is, in this preferred embodiment, insertable proximate to the irradiation site through a shielded, sterile port, the risk of incidental radiation exposure to other parts of the patient's body is significantly reduced.

Further, specificity in treating tumors may be achieved by tailoring the target and shield geometry and material at the emission site. This tailoring facilitates the control of energy and the spatial profile of the x-ray emission to ensure homogenous distribution of the radiation throughout the targeted tumor.

Figure 4:
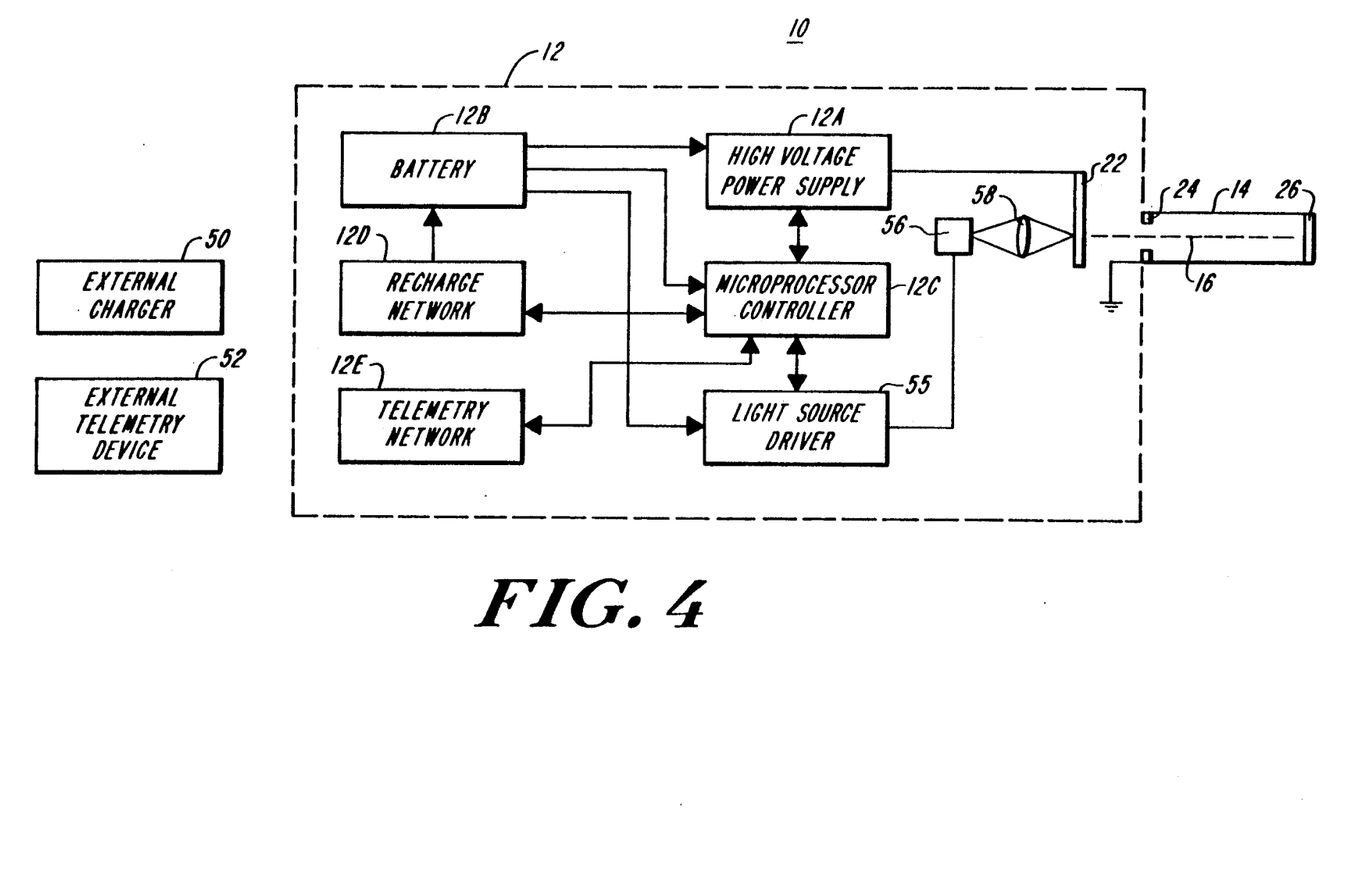
FIG. 4 is a schematic block diagram of the embodiment of FIG. 1.

FIG. 4 is a schematic representation of the fully implantable x-ray source apparatus 10 shown in FIG. 1. Enclosed within the housing 12 is the high voltage power supply 12A, a rechargeable battery 12B and a microprocessor-based controller 12C. The housing 12 also includes a recharge network 12D for the battery 12B, which is adapted for use with a transformer coupled to the external charger 50. A telemetry network 12E is adapted to be responsive to an external telemetry device 52 to function in the manner described below. In the illustrated apparatus 10, the electron beam generator includes a photocathode 22 driven by an associated light source driver 55 and diode laser 56 and associated lens assembly 58. In operation, laser 56 illuminates the photocathode 22, which in turn generates electrons which are then accelerated toward the anode 24. The anode 24 attracts the electrons, but passes them through its central aperture toward the target assembly 26. The microprocessor 12C controls the power supply 12A and light source driver 55 to dynamically adjust the cathode voltage, the electron beam current, and temporal parameters, or to provide pre-selected voltage, beam current, and temporal parameters.

In the illustrated embodiment, device 52 and network 12E cooperate to permit external control (dynamic or predetermined) control) over the power supply 12A and light source driver 55, and temporal parameters.

Figure 5A:
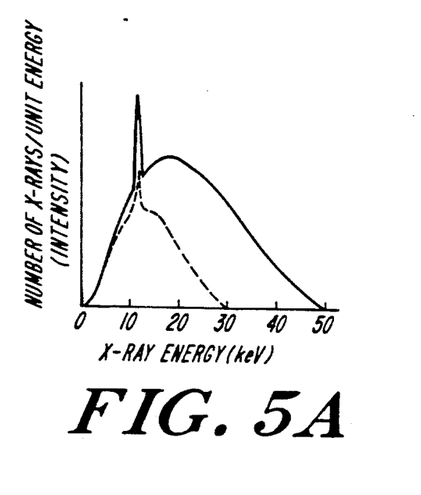
FIGS. 5A and 5B are graphical representations of the x-ray emission spectrum of tungsten- and molybdenum-targets, respectively.
Figure 5B:
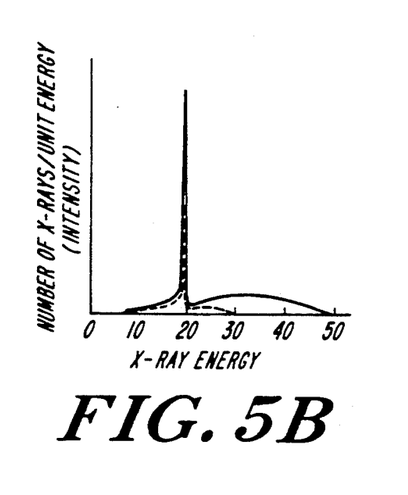

In an important aspect of the invention, the target assembly 26 may be shaped to emit x-rays in a radiation pattern having a predetermined spatial distribution, and in a predetermined spectral range. This target shaping may be achieved by selecting target materials of known characteristics. For example, as shown in FIGS. 5A and 5B, the emission spectrums for tungsten targets (FIG. 5A) and molybdenum targets (FIG. 5B) are distinct. FIG. 5A shows the x-ray emission spectrum from a tungsten target tube operating at 30 and 50 kV. Note that the bremsstrahlung spectrum predominates, and that x-rays are supplied in a wide energy range. FIG. 5B shows the emission spectrum from a molybdenum target tube, also operating at 30 and 50 kV. Note the near absence of bremsstrahlung x-rays. Note also that the change in tube potential from 30 to 50 kV results in a minor change in the shape of the emission spectrum from a molybdenum target x-ray tube. By selecting the target material, depending upon the type of penetration and the targeted region to be irradiated, the x-ray emission from target assembly 26 may effectively be shaped.

The emission spatial distribution may be also shaped by altering the geometric configuration of target assembly 26. By way of example, the emission element of the target assembly 26 may be shaped such that the electrons directed from the anode will be incident at a predetermined angle or may be selectively directed to different areas of the region from which emission is to occur. In a similar manner, "beam steering" may be used to direct the emitted electron beam to selected surfaces on the emission element, for example, where the target has different emission characteristics in different spatial regions. Control of the electron beam may be achieved under the control of telemetry, or by pre-programming the power source prior to implantation of the apparatus 10.

Figure 8:
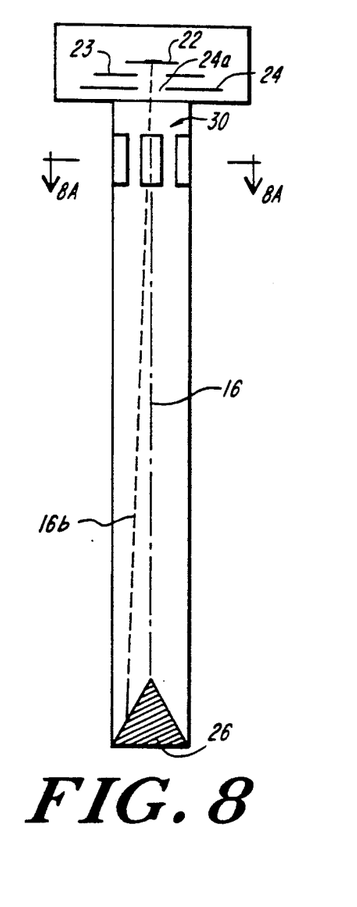
FIG. 8 is a perspective view of a beam steering assembly embodying the present invention.
Figure 8A:
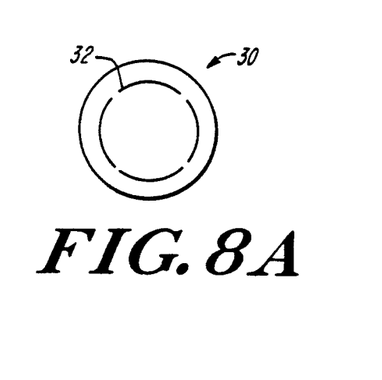

FIG. 8 shows an exemplary beam steering assembly. In the illustrated embodiment, the cathode 22 generates electrons in a manner consistent with the above-described embodiments. The electrons are accelerated through a focussing electrode 23 toward the anode 24, and pass through an aperture 24a toward the target assembly 26. Enroute to target assembly 26, the electrons pass through an electrostatic deflection assembly 30, shown in cross-section at FIG. 8A. The assembly includes four deflectors 32. By varying the voltages applied to the opposing pairs of the deflectors 32, the electrons of the beam entering the assembly along axis 16a are deflected, or "steered" as they travel toward the target assembly 26 along axis 16b.

In such a fashion, the electron beam may be steered to hit certain physical locations on a cone-shaped target assembly (FIG. 8), or a target of any other specific geometric configuration. By way of example, in the illustrated embodiment, a beam hitting the angled side of target assembly 26 will result in x-rays emitted off to that side, with little or no incidental radiation to the opposite side of the target assembly.

In another form of the beam-steering embodiment, the x-ray emission characteristics may be controlled by spatially varying the emission parameters (such as radiation peak vs. energy) of the target assembly. For example, by changing the emission peak (as a function of energy) at various points in the target assembly 26, for example, with a "bullseye" spatial pattern, the beam may be steered to regions of relatively high energy x-rayemission, or to regions of relatively low energy x-ray emission. Thus, the beam may be selectively directed to regions of the target assembly to achieve the required x-ray emission characteristic and direction.

In implantable configurations, the power supply 12A and target assembly 26 are preferably enclosed in a metal capsule to prevent current flow from the x-ray source to the patient. The closed housing 12 and probe 14 are, thus, encapsulated in a continuous outer shell of appropriate shielding material, such as those mentioned previously.

The high voltage power supply 12A in each of the illustrated embodiments preferably satisfies three criteria: 1) small in size; 2) high efficiency to enable the use of battery power; and 3) independently variable x-ray tube voltage and current to enable the unit to be programmed for specific applications. A high-frequency, switch-mode power converter is used to meet these requirements. The most appropriate topology for generating low power and high voltage is a flyback voltage converter working in conjunction with a high voltage, Cockroft-Walton-type multiplier. Low-power dissipation, switch-mode power-supply controller-integrated circuits (IC) are currently available for controlling such topologies with few ancillary components.

In order to provide active control of the x-rays, a preferred embodiment of the present invention establishes independent control of cathode voltage and current without the use of a grid electrode. In that form of the invention, an rf ohmic heating current is provided to a thermionic cathode 22 using a capacitively coupled 2 volt, 30 mA filament power supply floating at the cathode potential of 30 kV. In conventional power supplies for thermionic cathodes, a high voltage isolation transformer would be used to fulfill this function, but such components are quite bulky and thus inappropriate for a small apparatus. In contrast to the prior art, the present invention includes a high voltage power supply network which utilizes a dual chain of storage capacitors in the multiplier stage to conduct a radio-frequency (rf) current to the filament while maintaining high voltage direct current (dc) isolation. The system can be resonated with an inductor (L) at the rf current input, making control of the rf current level possible by changing either the amplitude or the frequency of the drive voltage. This change in the filament current changes the temperature of the filament, thus allowing control of the cathode current emission without changing the cathode-to-anode voltage.

Figure 6:
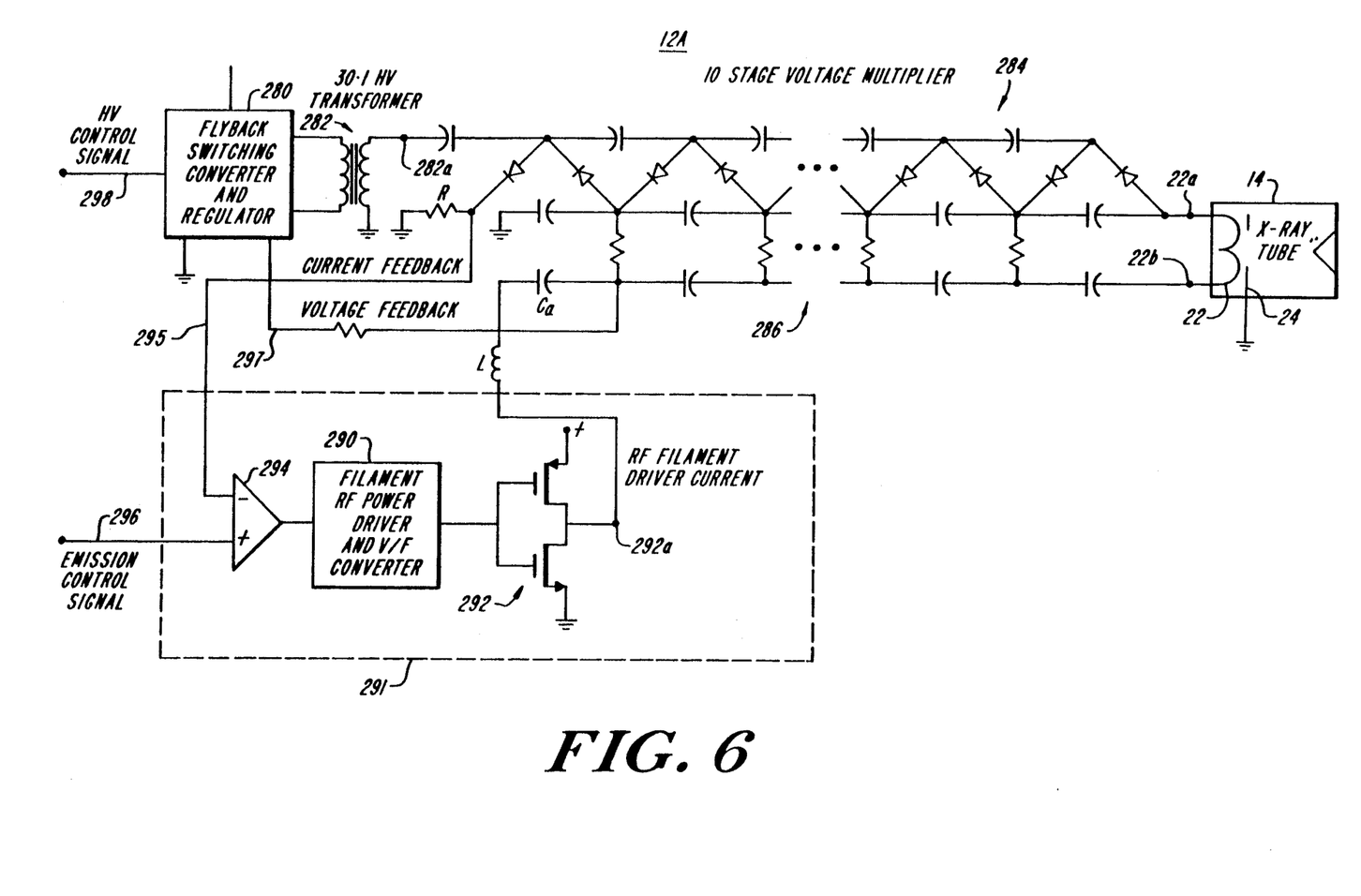
FIG. 6 is a detailed block diagram of the representative power supply of the embodiment of FIG. 1.
Figure 7:
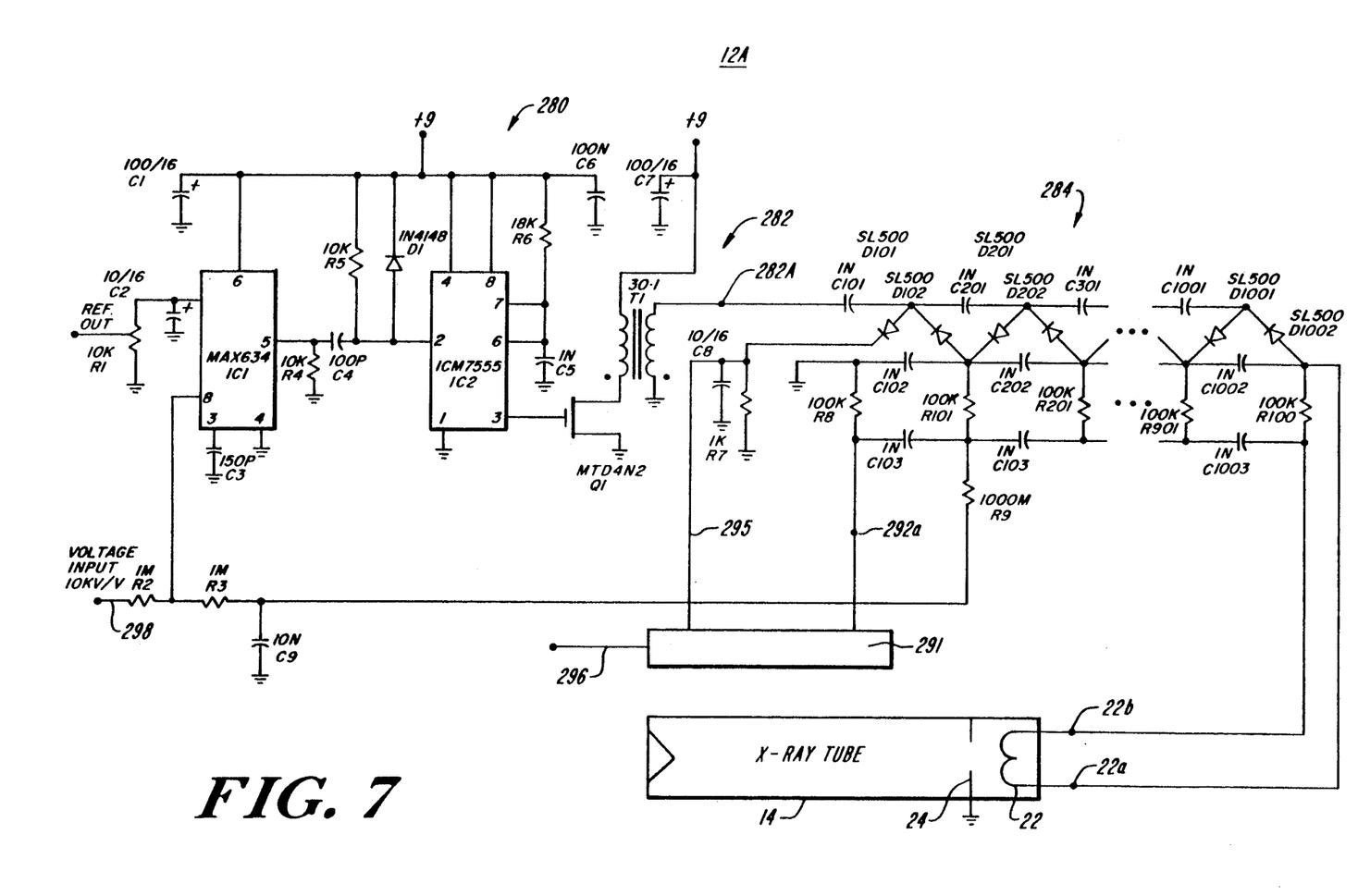
FIG. 7 is a detailed schematic diagram of the representative power supply of the embodiment of FIG. 1.

A preferred form of the power supply 12A is shown generally in FIG. 6, and in detailed schematic form in FIG. 7. As shown in FIG. 6, that embodiment includes a flyback switching converter and regulator 280, a 30:1 high voltage transformer 282 coupled to a control voltage (or high voltage multiplier input) terminal 282a, and a 10 stage voltage multiplier 284 coupled to a high voltage terminal 22a, and adapted to drive the filament of a thermionic emitter 22. A filament RF power driver and voltage-to-frequency (V/F) converter 290 and an associated RF filament driver 292 are coupled through current control terminal 292a and capacitor $C_o$ by way of a filament drive circuit 286 to the filament of emitter 22.

The multiplier 284 includes a set of 2n, i.e. 20, series connected diodes and first and second sets of n series coupled capacitors. The set of diodes establishes a unidirectional dc path between the high voltage terminal 22a, through a resistive element R, and to a reference (ground) potential.

The first set of capacitors is coupled between the junction of the first and second diodes (from terminal 22a) and the control voltage terminal 282a. The first n−1 capacitors of the first set are each coupled across associated successive pairs of diodes of the set of diodes starting with the second diode (from terminal 22a).

The second set of capacitors is coupled between the high voltage terminal 22a and a reference (ground) potential. The first n−1 capacitors of the second set are each coupled across associated successive pairs of diodes of the set of diodes, starting with the first diode (from terminal 284a).

The filament drive circuit 286 includes the voltage multiplier 284 (principally, the second set of capacitors) and a third set of series coupled capacitors. The third set of capacitors is coupled between the thermionic emitter terminal 22b and the current control terminal 292a. Each successive capacitor of the third set is associated with a correspondingly positioned capacitor in the second set, and the capacitor-to-capacitor junctions of the third set are resistively coupled to the correspondingly positioned junctions of the capacitor-to-capacitor junctions of the second set.

A difference amplifier 294 establishes a current feedback loop by driving the RF power driver and V/F converter 290 in response to the detected difference between a current feedback signal on line 295 and an applied emission control signal on line 296. The latter signal may be selectively controlled to establish a desired temporal variation in the x-ray tube cathode current in filament of emitter (thermionic cathode) 22.

A high voltage amplitude feedback loop is established by the switching converter and regulator 280 in response to the detected difference between a voltage feedback signal on line 297 and an applied high voltage control signal on line 298. The latter signal may be selectively controlled to establish a desired amplitude variation of the potential at the filament of emitter (thermionic cathode) 22. As shown in FIG. 7, the high voltage power supply 12A includes a low power CMOS negative boost converter controller IC 1 which controls the output voltage (at cathode 22) by varying the density of constant energy pulses from the power transformer 282. The output voltage is electrically Compared to a programming voltage (from line 298) and, if the output voltage is too low, the frequency of the energy pulses is increased. The control pulse from controller IC 1 is fed to a low power CMOS timer IC 2 where the pulse is shortened and buffered to a level appropriate for driving a high voltage flyback converter (Q1 and T1). High voltage pulses are generated on the secondary of transformer 282 (T1) that are rectified by the n=10 stage diode multiplier 284. Voltage feedback is preferably taken from the first stage of the multiplier 284, since this uses less power and reduces the voltage stress on the feedback resistor R9. The output voltage of the multiplier 284 is well correlated with the voltage at the first stage due to the clamping nature of this type of multiplier.

Cathode emission current control is achieved by sensing the current at the bottom (at R7 and C8) of the n diode chain of multiplier 284, since the only dc path for the cathode current is through the 2n diodes of multiplier 284. This enables sensing the current of the cathode near ground potential instead of at the output potential, which may be 30 kV, for example. This sensed current is converted to a voltage and compared to the emission current programming voltage (signal from line 296) at block 291. If in error, the voltage or frequency of the filament driver is adjusted accordingly in a closed loop manner.

With this configuration, independent control of cathode voltage and current is achieved while maintaining a power efficiency of greater than 70% and a volume of less than 3 cubic inches, meeting the desired design goals of the system.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An x-ray source comprising:
   A. a programmable power supply including drive means for establishing an output voltage having a peak value in the approximate range of 10 kV to 90 kV;
   B. beam generator means responsive to said output voltage for emitting electrons to generate an electron beam along a beam path, said beam being characterized by a current in the approximate range of 1 nA to 100 µA,
   wherein at least one of the amplitude of said output voltage and the magnitude of said current can be varied over time in response to a programming operation; and further comprising:
   C. a target assembly positioned in said beam path, said target including at least one x-ray emission element adapted to emit x-rays in a predetermined spectral range in response to incident electrons from said beam;
   D. field distribution means for establishing an x-ray radiation pattern having a spatial distribution, said spatial distribution being at least in part external to said source, and
   E. a controller including means for user-controlled adjustment of at least one of the amplitude of said output voltage and the magnitude of said current.

2. An x-ray source according to claim 1 wherein said target assembly includes at least one emission element.

3. An x-ray source comprising:
   A. a power supply including drive means for establishing an output voltage having a peak value in the approximate range of 10 kV to 90 kV,
   wherein the amplitude of said output voltage is a predetermined function of time;
   B. beam generator means responsive to said output voltage for emitting electrons to generate an electron beam along a beam path, said beam being characterized by a current in the approximate range of 1 nA to 100 µA,
   wherein the magnitude of said current is a predetermined function of time;
   C. a target assembly positioned in said beam path, said target including at least one x-ray emission element adapted to emit x-rays in a predetermined spectral range in response to incident electrons from said beam; and
   D. field distribution means for establishing an x-ray radiation pattern having a spatial distribution, said spatial distribution being at least in part external to said source,
   wherein said beam generator means includes a photocathode, an anode adapted to attract electrons emitted from said photocathode, and means responsive to said output voltage coupled across the photocathode and anode for establishing an accelerating electric field between said photocathode and said anode, and
   wherein said anode is positioned between said photocathode and said target, said anode including an aperture through which said electrons pass.

4. An x-ray source comprising:
   a power supply including drive means for establishing an output voltage having a peak value in the approximate range of 10 kV to 90 kV, wherein the amplitude of said output voltage is a predetermined function of time;
   beam generator means responsive to said output voltage for emitting electrons to generate an electron beam along a beam path, said beam being characterized by a current in the approximate range of 1 nA to 100 µA, wherein the magnitude of said current is a predetermined function of time;
   a target assembly positioned in said beam path, said target including at least one x-ray emission element for emitting x-rays in a predetermined spectral range in response to incident electrons from said beam; and
   field distribution means for establishing an x-ray radiation pattern having a spatial distribution, said spatial distribution being at least in part external to said source, wherein said beam generator means includes a thermionic emitter, an anode and means responsive to said output voltage for establishing an accelerating electric field between said thermionic emitter and said anode, and wherein said thermionic emitter includes a thermionic cathode having a first terminal and a second terminal, and said drive means comprises:

A. a voltage multiplier network having a control voltage terminal and having a high voltage terminal coupled to said first terminal of said thermionic emitter, said voltage multiplier network including first circuit means coupled between said control voltage terminal and said high voltage terminal and responsive to an applied control voltage at said control voltage terminal for establishing said output voltage at said high voltage terminal, B. a thermionic emitter heater network having a current control terminal and including second circuit means capacitively coupled to said current control terminal for driving an rf ohmic heating current through said thermionic cathode in response to a current control signal applied at said current control terminal.

5. An x-ray source according to claim 4 wherein said beam generator includes a focussing electrode.

6. An x-ray source according to claim 5 wherein said first circuit means comprises:
   i. a set of 2n series coupled diodes establishing a unidirectional dc path from said high voltage terminal and extending through the first diode, the second diode, and the remaining diodes in succession of said set of diodes, and then through a resistive element to a reference potential, where n is an integer,
   ii. a first set of n series coupled capacitors coupled between the junction between said first and second diodes and said control voltage terminal, wherein each successive capacitor of the first n−1 capacitors of said first set is coupled across an associated successive pair of diodes of said set of diodes, starting with said second diode,
   iii. a second set of n series coupled capacitors coupled between said high voltage terminal and a reference potential, wherein each successive capacitor of the first n−1 capacitors of said second set is coupled across an associated successive pair of diodes of said set of diodes, starting with said first diode, and wherein said second circuit means comprises:
   i. said first circuit means,
   ii. a third set of n series coupled capacitors coupled between a current control terminal and said second terminal of said thermionic cathode, wherein each successive capacitor of said third set is associated with a correspondingly positioned capacitor of said second set, and the capacitor-to-capacitor junctions of said third set are resistively coupled to the correspondingly positioned capacitor-to-capacitor junctions of said second set, and
   iii. an rf current source coupled to said current control terminal, said current source including means for driving said rf ohmic heating current through third set of capacitors, said thermionic cathode, and said second circuit means to said reference potential.

7. An x-ray source according to claim 6 further comprising a current feedback means for sensing the level of said rf current and for controlling said current level in response to said current control signal.

8. An x-ray source according to claim 7 further comprising a voltage feedback means for sensing the voltage level at said high voltage terminal and for controlling said voltage level in response to said control voltage signal.

9. An x-ray source according to claim 6 further comprising a voltage feedback means for sensing the voltage level at said high voltage terminal and for controlling said voltage level in response to said control voltage signal.

10. An x-ray source comprising:
A. a power supply including drive means for establishing an output voltage having a peak value in the approximate range of 10 kV to 90 kV, wherein the amplitude of said output voltage is a predetermined function of time;

B. beam generator means responsive to said output voltage for emitting electrons to generate an electron beam along a beam path, said beam being characterized by a current in the approximate range of 1 nA to 100 μA, wherein the magnitude of said current is a predetermined function of time;

C. a target assembly positioned in said beam path, said target including at least one x-ray emission element adapted to emit x-rays in a predetermined spectral range in response to incident electrons from said beam; and D. field distribution means for establishing an x-ray radiation pattern having a spatial distribution, said spatial distribution being at least in part external to said source, further comprising a closed housing, wherein said beam generator means and said target assembly are disposed within said housing, said housing having a window on one outer surface thereof, whereby said emitted x-rays are emitted through said window, and wherein said field distribution means comprises a shield assembly including means for restricting the x-rays emitted by said emission element, whereby said radiation pattern is restricted to have said spatial distribution.

11. An x-ray source according to claim 10 wherein said power supply further includes selectively operable control means including means for selectively controlling the amplitude of said output voltage.

12. An x-ray source according to claim 1 wherein said power supply further includes selectively operable control means further includes means for selectively controlling the amplitude of said beam generator current.

13. An x-ray source comprising:
A. a power supply including drive means for establishing an output voltage having a peak value in the approximate range of 10 kV to 90 kV, wherein the amplitude of said output voltage is a predetermined function of time;

B. beam generator means responsive to said output voltage for emitting electrons to generate an electron beam along a beam path, said beam being characterized by a current in the approximate range of 1 nA to 100 μA, wherein the magnitude of said current is a predetermined function of time;

C. a target assembly positioned in said beam path, said target including at least one x-ray emission element adapted to emit x-rays in a predetermined spectral range in response to incident electrons from said beam; and D. field distribution means for establishing an x-ray radiation pattern having a spatial distribution, said spatial distribution being at least in part external to said source, further comprising a closed housing, wherein said beam generator means and said target assembly are disposed within said housing, said housing having a window on one outer surface thereof, whereby said emitted x-rays are emitted through said window, and further comprising an elongated cup-shaped sheath and associated skin entry port, said sheath and port having a biocompatible outer surface, and wherein at least the portion of said housing, including said window, is insertable into the interior of said sheath.

14. An x-ray source according to claim 13 wherein said field distribution means comprises a shield assembly including means for restricting the x-rays emitted by said emission element, whereby said radiation pattern is restricted to have said spatial distribution.

15. An x-ray source according to claim 13 wherein said power supply further includes selectively operable control means including means for selectively controlling the amplitude of said output voltage.

16. An x-ray source according to claim 13 wherein said power supply further includes selectively operable control means further includes means for selectively controlling the amplitude of said beam generator current.

17. An x-ray source comprising:

A. a power supply including drive means for establishing an output voltage having a peak value in the approximate range of 10 kV to 90 kV, wherein the amplitude of said output voltage is a predetermined function of time;

B. beam generator means responsive to said output voltage for emitting electrons to generate an electron beam along a beam path, said beam being characterized by a current in the approximate range of 1 nA to 100 μA, wherein the magnitude of said current is a predetermined function of time;

C. a target assembly positioned in said beam path, said target including at least one x-ray emission element adapted to emit x-rays in a predetermined spectral range in response to incident electrons from said beam; and D. field distribution means for establishing an x-ray radiation pattern having a spatial distribution, said spatial distribution being at least in part external to said source, further comprising a closed housing, wherein said power supply, said beam generator means, and said target assembly are disposed within said housing, said housing having a window on one outer surface thereof, whereby said emitted x-rays are emitted through said window, and wherein at least a portion of said closed housing has a biocompatible outer surface.

18. An x-ray source according to claim 17 wherein said field distribution means comprises a shield assembly including means for restricting the x-ray radiation emitted by said emission element, whereby said radiation pattern is restricted to have said spatial distribution.

19. An x-ray source according to claim 17 wherein said field distribution means comprises said x-ray emission element and a beam steering assembly, wherein said x-ray emission element has a predetermined shape and said beam steering assembly includes means for steering said electron beam to selected surface regions of said emission element whereby said emission element emits an x-ray radiation pattern having said spatial distribution.

20. An x-ray source according to claim 17 further comprising temporal control means for establishing an x-ray pattern having a predetermined temporal intensity variation.

21. An x-ray source according to claim 20 wherein said temporal control means includes a programmable means for controlling time variation in the amplitude of said output voltage.

22. An x-ray source according to claim 20 wherein said temporal control means includes a programmable means for controlling time variation in the amplitude of said beam generator current.

23. An x-ray source according to claim 17 further comprising:

A. means for generating a signal representative of a desired x-ray radiation pattern;

B. means associated with said power supply and responsive to said signal to control said power supply to generate said output voltage.

24. An x-ray source according to claim 23 wherein said power supply further includes selectively operable control means including means for selectively controlling the amplitude of said output voltage.

25. An x-ray source according to claim 23 wherein said selectively operable control means further includes means for selectively controlling the amplitude of said beam generator current.

26. An x-ray source comprising:

A. a power supply including drive means for establishing an output voltage having a peak value in the approximate range of 10 kV to 90 kV, wherein the amplitude of said output voltage is a predetermined function of time;

B. beam generator means responsive to said output voltage for emitting electrons to generate an electron beam along a beam path, said beam being characterized by a current in the approximate range of 1 nA to 100 μA, wherein the magnitude of said current is a predetermined function of time;

C. a target assembly positioned in said beam path, said target including at least one x-ray emission element adapted to emit x-rays in a predetermined spectral range in response to incident electrons from said beam; and D. field distribution means for establishing an x-ray radiation pattern having a spatial distribution, said spatial distribution being at least in part external to said source, wherein said target assembly includes a plurality of emission elements, and the x-ray emission characteristic of at least one of said emission elements is selectively controllable independent of each other of said emission elements.

27. An x-ray source according to claim 26 wherein each of said elements have predetermined shape characteristics.

28. A method of treating tumors in a patient, comprising the steps of:
   A. identifying and locating a tumor in vivo;
   B. implanting at least a portion of an adjustable x-ray radiation source in said patient proximate to said tumor; and
   C. controlling said source to generate an x-ray radiation pattern, characterized by a spatial and temporal distribution, to selectively irradiate said tumor.

29. A method according to claim 28 further comprising the step of controlling said temporal distribution of said x-ray radiation pattern.

30. A method according to claim 28 further comprising the step of controlling said spatial distribution of said x-ray radiation pattern.

31. An x-ray source according to claims 1 or 3 or 4 or 10 or 13 or 17 or 26 wherein said power supply further includes selectively operable control means for selectively controlling the amplitude of said output voltage.

32. An x-ray source according to claims 1 or 3 or 4 or 10 or 13 or 17 or 26 wherein power supply further includes said selectively operable control means for selectively controlling the amplitude of said beam generator current.

33. An x-ray source according to claims 1 or 3 or 4 or 10 or 13 or 17 or 26 further comprising a diamond window allowing passage of said x-rays to a region to be irradiated.

* * * * *